United States Patent [19]

Choksi et al.

[11] 4,255,996

[45] Mar. 17, 1981

[54] NEEDLE DESTROYER WITH IMPROVED MECHANICAL ADVANTAGE

[75] Inventors: Pradip V. Choksi, Northridge, Calif.; William D. Christoffel, Two Rivers, Wis.; Christopher J. C. Edwards, Woodland Hills, Calif.

[73] Assignee: American Hospital Supply Corporation, Evanston, Ill.

[21] Appl. No.: 97,263

[22] Filed: Nov. 19, 1979

[51] Int. Cl.[3] .................. B23D 21/06; B23D 17/00
[52] U.S. Cl. ............................ 83/140; 83/167; 83/580; 83/599; 83/925 R
[58] Field of Search ............... 83/167, 199, 200, 140, 83/580, 599, 598, 925 R; 30/131

[56] References Cited

U.S. PATENT DOCUMENTS

| | | |
|---|---|---|
| 3,404,593 | 10/1968 | Arcarese et al. ............... 83/925 R |
| 3,469,750 | 9/1969 | Vanderbeck ..................... 83/925 R |
| 3,585,835 | 6/1971 | Clement ........................... 83/925 R |
| 3,736,824 | 6/1973 | Dunnican ......................... 83/167 |
| 3,785,233 | 1/1974 | Robinson ......................... 83/167 |
| 3,914,865 | 10/1975 | Oakes .............................. 30/131 |

Primary Examiner—J. M. Meister
Attorney, Agent, or Firm—Larry N. Barger

[57] ABSTRACT

A device having one embodiment for severing a hypodermic needle at its hub and cannula with a single motion. The device has hub and cannula cutters that are joined at a slidable joint and pivoted at noncoaxial pivot points to provide increased mechanical advantage to the cannula cutter. In another preferred embodiment, the same type cutting mechanism has its cutters spaced so as to sever a hypodermic syringe barrel and a cannula of a needle attached to the syringe barrel in a single motion.

28 Claims, 4 Drawing Figures

U.S. Patent  Mar. 17, 1981  4,255,996
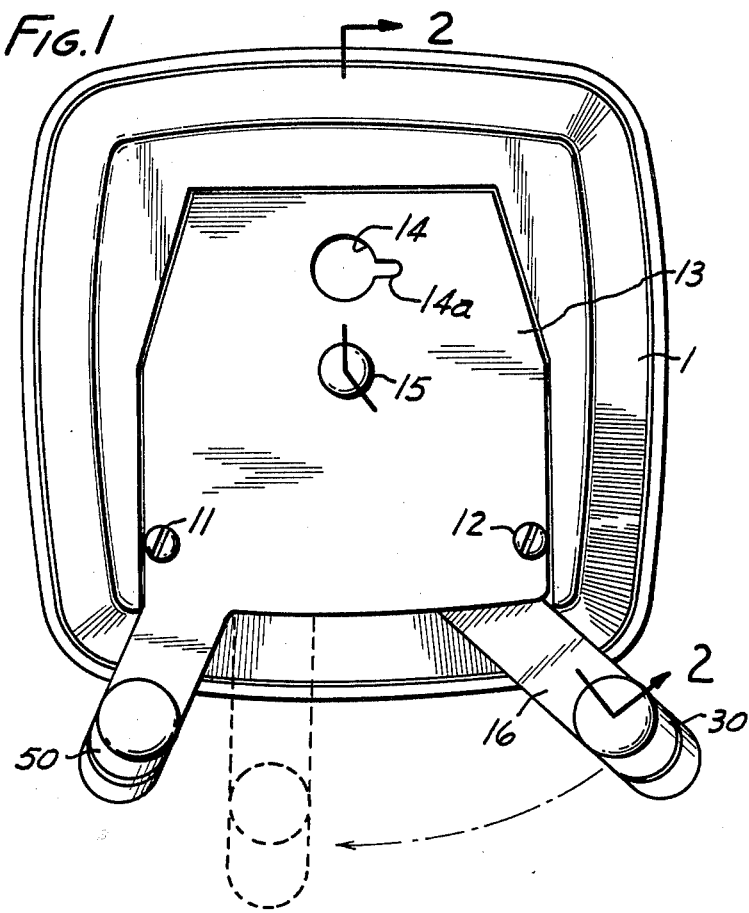
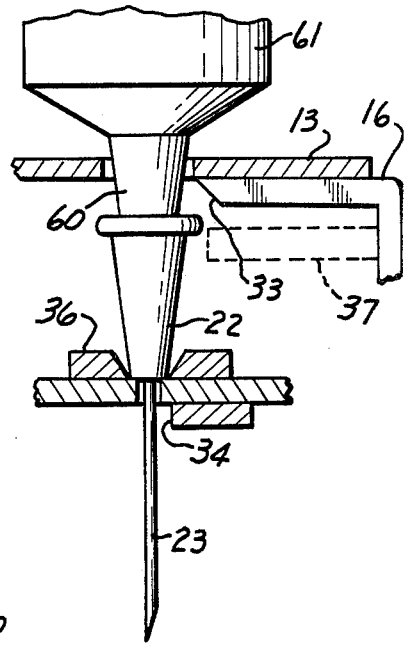
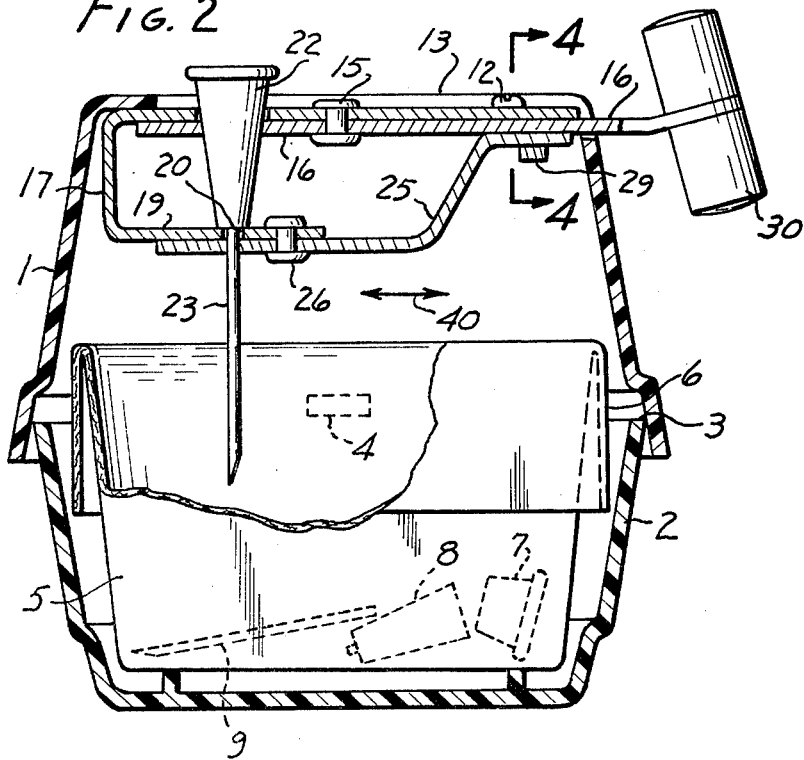

NEEDLE DESTROYER WITH IMPROVED MECHANICAL ADVANTAGE

BACKGROUND

U.S. Pat. No. 3,914,865 describes a device that cuts both the metal cannula and attached plastic hub or syringe barrel with separately actuated cutters. Another device marketed by Becton Dickinson under the trademark DESTRUCLIP is a box-like device that cuts the cannula and syringe barrel or hub in separately actuated cutting steps. The reason these devices required two cutting motions was because the stainless steel cannula required a very high cutting force over a small distance; i.e., diameter of cannula. Conversely, the much larger diameter thermoplastic hub or barrel required a greater distance of travel during its cutting step, but required less force because the thermoplastic was softer than the metal cannula. This double cutting motion required by an operator was tedious in that there were two manual cutting motions required, as well as two insertions of the needle or syringe into the device.

Other syringe and needle destroyers such as in U.S. Pat. Nos. 3,404,593 and 3,785,233, which made both cuts a simultaneous operator motion, were cumbersome. They required very large levers to get both the long distance cutter travel for severing the large diameter hub or syringe barrel and also get the required cutting force for the metal cannula. Such units usually require the full arm motion of the operator.

SUMMARY OF THE INVENTION

The present invention overcomes the above problems with previous devices by providing a very compact needle destroyer in which a small amount of force (such as squeezing between thumb and forefinger) can easily move cutters to sever both a large diameter thermoplastic hub or syringe barrel, as well as a stainless steel cannula. The cutters are pivoted and interconnected in a manner that increases the mechanical advantage of the cannula cutter.

THE DRAWINGS

FIG. 1 is a top plan view of the needle destroyer;

FIG. 2 is a sectional view taken along line 2—2 of FIG. 1 showing a first embodiment of the destroyer cutting a cannula and hub;

FIG. 3 is an enlarged view taken along a direction 90° to the view of FIG. 2, but showing a second embodiment of the destroyer which cuts the cannula and syringe barrel; and FIG. 4 is an enlarged view taken along line 4—4 of FIG. 2.

DETAILED DESCRIPTION

In FIG. 1, the needle destroyer includes a housing with a top portion 1 and a bottom portion 2 that is separable along a joint 3. A latch means shown generally at 4 maintains the top and bottom of the housing connected together during use. Inside the housing is a removable box 5 with a lid 6. Preferably, the box 5 extends above joint 3. The syringe destroyer severs a thermoplastic hub or syringe barrel, as well as a metal cannula so that the severed pieces, shown as 7, 8, and 9, can fall into box 5. Periodically the box can be removed, sealed, and then disposed of.

Secured to top 1, such as by screws 11 and 12, is a cutting mechanism that includes a hub shear plate 13 with a needle opening 14. Preferably, needle opening 14 has a slot 14a into which the metal cannual can enter to prevent dulling the hub or syringe barrel cutter (which might not be hardened) or cause the cannula to bend over and not sever. This might occur when the needle was not inserted far enough into the destroyer. A handle 50 is rigidly attached to shearing plate 13. A pivot pin 15 pivotally mounts a hub cutter 16 to hub shearing plate 13.

Hub shearing plate 13 is connected through a U-shaped end portion 17 to a cannula shear plate 19 that includes an opening 20 for receiving a cannula. As shown in FIG. 2, the hypodermic needle, including a thermoplastic hub 22 and stainless steel cannula 23, has been inserted in the needle destroyer. In this first embodiment, the spacing between the cutter is such that the cannula and hub are cut.

A cannula cutter 25 is pivotally connected through a pivot pin 26 to cannula shear plate 19. A loop member 29 slidably connects the hub and cannula cutters. Thus as handle 30, which is connected to an extension of cutter 16, is moved in FIG. 1 to its dotted position, the hub and cannula cutters simultaneously sever both the hub and cannula with this one manual motion. Because pivot 15 is spaced further away from the needle than pivot 26, the hub cutter travels a greater distance than does the cannula cutter at their respective cutting edges. The sliding joint at 29 permits the two cutters to simultaneously pivot, although the respective pivot points at 15 and 26 are laterally offset; i.e., noncoaxial. The pivot pin 26, which is very close to cannula 23, has a very large mechanical advantage in severing the metal cannula. However, it has a small distance of travel because of the small diameter of cannula 23.

Because hub 22 or syringe barrel is of a thermoplastic material, a sharpened cutting edge 33 is preferred. A blunt, preferably hardened, shearing edge 34 is preferred on the cannula cutter. A very sharp, beveled edge would simply dull when abutting the metal cannula. It is preferable to include a funnel member 36 to help guide the cannula into its opening. Also, a spring member 37 can be used to help sweep away the middle portion of the severed needle to prevent its clogging the cutting mechanism. In FIG. 3, the preferred embodiment of the cutter is shown where the cutters sever the metal cannula and syringe barrel, such as at adapter 60. If desired for small syringes, the cutters could be spaced so the top cutter severs the main body 61 of the barrel.

During the single squeezing motion between handles 30 and 50, the cannula cutter laterally slides, as shown by arrows 40, relative to the hub cutter and this combines with the offset pivots 15 and 26 to provide the improved mechanical advantage. In describing the needle destroyer of this invention, a hypodermic needle has been used for illustrative purposes. It is to be understood that this destroyer can also be used to destroy cannulas attached directly to syringe barrels, for such barrels would form a portion of the hub.

In the foregoing description, a specific example of the needle destroyer has been used to illustrate the invention. However, it is understood by those skilled in the art that certain modifications can be made to this example without departing from the spirit and scope of the invention.

We claim:

1. A needle destroyer with a common opening for receiving and severing both the hub and cannula of a needle, wherein the improvement comprises: a hub cutter and a cannula cutter on the destroyer joined to each other at a movable joint providing a greater mechanical advantage at the cannula cutter than at the hub cutter when the joined cutters are actuated.

2. A needle destroyer as set forth in claim 1, wherein the hub cutter has a cutting edge for severing thermoplastic.

3. A needle destroyer as set forth in claim 2, wherein the cutting edge is sharp.

4. A needle destroyer as set forth in claim 1, wherein the cannula cutter has a cutting edge for severing metal.

5. A needle destroyer as set forth in claim 4, wherein the cutting edge is blunt.

6. A needle destroyer as set forth in claim 1, wherein there is a sliding joint connecting the two cutters.

7. A needle destroyer as set forth in claim 1, wherein each cutter is pivoted to the destroyer and the pivots are noncoaxial.

8. A needle destroyer as set forth in claim 7, wherein the destroyer has spaced apart hub and cannula shear plates, and the hub and cannula cutters are respectively pivoted to these plates.

9. A needle destroyer as set forth in claim 1, wherein the joined cutters have a common actuating handle.

10. A needle destroyer as set forth in claim 1, wherein the destroyer has an openable housing with a removable receptacle for receiving severed pieces of a needle.

11. A needle destroyer as set forth in claim 1, wherein the destroyer includes a funnel structure for guiding insertion of the needle into the destroyer.

12. A needle destroyer as set forth in claim 1, wherein the destroyer has sweeping means to remove severed needle portions from the cutters.

13. A needle destroyer as set forth in claim 12, wherein the sweeping means is a spring.

14. A needle destroyer with a common opening for receiving and severing both the hub and cannula of a needle, wherein the improvement comprises: a hub cutter and a cannula cutter pivotally connected to the destroyer at pivot points that are noncoaxial, and the cutters are joined to a common actuating handle providing a greater mechanical advantage at the cannula cutter than at the hub cutter when the handle is moved.

15. A syringe and needle destroyer with a common opening for receiving and severing both a syringe and an attached needle's cannula, wherein the improvement comprises: a syringe cutter and a cannula cutter on the destroyer joined to each other at a movable joint providing a greater mechanical advantage at the cannula cutter than at the syringe cutter when the joined cutters are actuated.

16. A syringe and needle destroyer as set forth in claim 15, wherein the syringe cutter has a cutting edge for severing thermoplastic.

17. A syringe and needle destroyer as set forth in claim 16, wherein the cutting edge is sharp.

18. A syringe and needle destroyer as set forth in claim 15, wherein the cannula cutter has a cutting edge for severing metal.

19. A syringe and needle destroyer as set forth in claim 18, wherein the cutting edge is blunt.

20. A syringe and needle destroyer as set forth in claim 15, wherein there is a sliding joint connecting the two cutters.

21. A syringe and needle destroyer as set forth in claim 15, wherein each cutter is pivoted to the destroyer and the pivots are noncoaxial.

22. A syringe and needle destroyer as set forth in claim 21, wherein the destroyer has spaced apart syringe and cannula shear plates, and the syringe and cannula cutters are respectively pivoted to these plates.

23. A syringe and needle destroyer as set forth in claim 15, wherein the joined cutters have a common actuating handle.

24. A syringe and needle destroyer as set forth in claim 15, wherein the destroyer has an openable housing with a removable receptacle for receiving severed pieces of the syringe and needle.

25. A syringe and needle destroyer as set forth in claim 15, wherein the destroyer includes a funnel structure for guiding insertion of the needle into the destroyer.

26. A syringe and needle destroyer as set forth in claim 15, wherein the destroyer has sweeping means to remove severed syringe and needle portions from the cutters.

27. A syringe and needle destroyer as set forth in claim 26, wherein the sweeping means is a spring.

28. A syringe and needle destroyer with a common opening for receiving and severing both a syringe and an attached needle's cannula, wherein the improvement comprises: a syringe cutter and a cannula cutter pivotally connected to the destroyer at pivot points that are noncoaxial, and the cutters are joined to a common actuating handle providing a greater mechanical advantage at the cannula cutter than at the syringe cutter when the handle is moved.

* * * * *